United States Patent [19]
Glazer et al.

[11] Patent Number: 5,977,344
[45] Date of Patent: *Nov. 2, 1999

[54] DNA COMPLEXES WITH DYES DESIGNED FOR ENERGY TRANSFER AS FLUORESCENT MARKERS

[75] Inventors: Alexander M. Glazer, Orinda; Scott C. Benson, Albany, both of Calif.

[73] Assignee: The Regents of the University of California, Berkeley, Calif.

[ * ] Notice: This patent is subject to a terminal disclaimer.

[21] Appl. No.: 08/965,833

[22] Filed: Nov. 7, 1997

Related U.S. Application Data

[63] Continuation of application No. 08/771,443, Dec. 20, 1996, Pat. No. 5,767,267, which is a continuation of application No. 08/340,749, Jan. 23, 1995, Pat. No. 5,646,264, which is a division of application No. 08/009,704, Jan. 27, 1993, Pat. No. 5,401,847, which is a continuation-in-part of application No. 07/831,823, Feb. 6, 1992, abandoned, which is a continuation-in-part of application No. 07/493,307, Mar. 14, 1990, abandoned.

[51] Int. Cl.$^6$ .............................. C07H 21/04; C07H 21/02
[52] U.S. Cl. ....................................... 536/25.32; 536/26.6
[58] Field of Search ............................... 435/6; 536/25.32, 536/25.4, 26.6

[56] References Cited

U.S. PATENT DOCUMENTS

| 4,737,454 | 4/1988 | Dattagupta et al. ................. 435/6 |
| 5,646,264 | 7/1997 | Glazer et al. ................. 536/25.32 |
| 5,767,267 | 6/1998 | Glazer et al. ................. 536/25.32 |

OTHER PUBLICATIONS

Markovits (Analy. Biochem. 94:259–264), 1979.
Gawgain et al (Biochem; 17:5078–5088, 1978.

Primary Examiner—Eggerton A. Campbell
Attorney, Agent, or Firm—Bret E. Field; Bozicevic, Field & Francis, LLP

[57] ABSTRACT

Heteromultimeric fluorophores are provided for binding to DNA, which allow for the detection of DNA in electrical separations and preparation of probes having high-fluorescent efficiencies and large Stokes shifts. In addition, by appropriate choice of fluorescent molecules, one can use a single narrow wavelength band excitation light source, while obtaining fluorescent emissions having sufficient separation to be readily discriminated.

3 Claims, 2 Drawing Sheets

DNA COMPLEXES WITH DYES DESIGNED FOR ENERGY TRANSFER AS FLUORESCENT MARKERS

CROSS-REFERENCE TO RELATED APPLICATIONS

This application is a continuation of 08/771,443, filed Dec. 20, 1996, now U.S. Pat. No. 5,767,267, which is a continuation of 08/340,749, filed on Jan. 23, 1995, now U.S. Pat. No. 5,646,264, which is a divisional of 009,704, filed on Jan. 27, 1993, now U.S. Pat. No. 5,401,847, which is a CIP of 07/831,823, filed on Feb. 6, 1992, now abandoned, which is a CIP of 07/493,307, filed on Mar. 14, 1990 abandoned.

CROSS-REFERENCE TO GOVERNMENT GRANT

This invention was made with Government support under Grant Contract No. DE-FG-91ER61125 awarded by the Department of Energy. The Government has certain rights in this invention.

INTRODUCTION

1. Technical Field

The field of this invention is fluorescent compositions.

2. Background

Detection of fluorescent signals finds wide application in a variety of situations and under a variety of conditions. Fluorescence has many advantages as a means of generating a detectable signal. Fluorescence does not suffer from the many disadvantages of a radioactive label, while in many cases it provides for a high level of sensitivity. Instrumentation for detection of fluorescence is readily available and fluorescent labels have found application in such diverse situations as immunodiagnostics, detection of nucleic acid bands and protein bands in gel electrophoresis and in fluorescence activated cell sorters. The sensitivity of the fluorescent signal depends upon a number of factors: the possibility of self-quenching; the effect of other molecules associated with the fluorescent molecule on the quantum efficiency of the fluorescence; the effect of the medium on the quantum efficiency and fluorescence characteristics of the fluorescer; the stability of the fluorescer to light; the ability to remove background fluorescence; and the nature of the light source.

For many applications one wishes to have a number of distinguishable fluorescers, so that one can detect different characteristics of a system. For example, in the FACS, there may be an interest in identifying the presence of two characteristics of the cell or other composition. In the hybridization of DNA, one may wish to observe two different DNA sequences, as observed in a gel, on a plate, or the like. Frequently, it is very difficult to obtain fluorescers having emission maxima which are sufficiently different so as to be differentiable while allowing for excitation at the same wave length. There is, therefore, substantial interest in identifying fluorescent markers which permit multiplex determinations by providing for readily differentiable, fluorescent emission maxima, while allowing for excitation with a narrow band radiation source.

RELEVANT LITERATURE

The following references describe DNA intercalating fluorescent dimers and their physical characteristics: Gaugain et al., *Biochemistry* 17, 5071–5078, 1978; Gaugain et al., *Biochemistry* 17, 5078–5088, 1978; Markovits et al., *Anal. Biochemistry* 94, 259–269, 1979; Markovits *Biochemistry* 22, 3231–3237, 1983; and Markovits et al., *Nucl. Acids Res.* 13, 3773–3788, 1985. Interaction of various intercalating compounds with nucleic acids is reviewed by Berman and Young, *Ann. Rev. Biophys. Bioeng.* (1986) 10:87–224. Retention of ethidium bromide on electrophoresis of the dye with DNA or RNA is described by Angemuller and Sayavedra-Soto, Biotechnicues 8, 36, 1990 and Rosen and villa-Komaroff, *Focus* 12, 23, 1990 (see also Glazer et al. (1990) *Proc. Natl. Acad. Sci. USA* 87:3851–3855; Rye et al. (1991) *Nucl. Acids Res.* 19:327–333; Quesada et al. (1991) *BioTechniques* 10:616–625; Rye et al. (1992) *Nucl. Acids Res.* 20:2803–2812.

SUMMARY OF THE INVENTION

Novel fluorescent compositions and their use are provided, where the fluorescent compositions are characterized by strongly binding to double stranded DNA having a multiplicity of positive charges, having at least two fluorophoric moieties, where one moiety is capable of efficiently quenching the fluorescence (excitation energy) of the moiety emitting at a lower wave length; the intercalated fluorescent composition provides for emission efficiencies substantially in excess of the parent fluorophore; and ratios of observed fluorescence emission between the higher wave length emitting fluorophore and the lower wave length emitting fluorophore are at least about 1.2 to 1. These compositions find use as fluorescent markers for DNA, in combination with DNA as labels for other molecules, and in the analysis of various systems, where multiplex fluorescent analysis is desired.

DESCRIPTION OF THE SPECIFIC EMBODIMENTS

Figure 1:
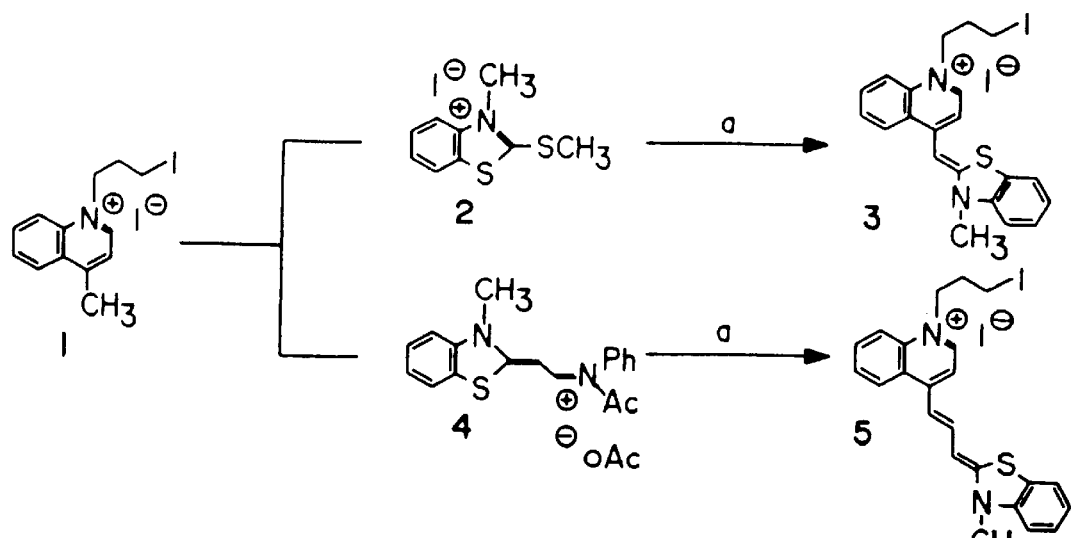
FIG. 1 is a synthetic scheme for the synthesis of thiazole monomer intermediates.

Novel methods are provided employing heterodimeric fluorescent compounds, by themselves or intercalated into double stranded nucleic acids, where the compositions are characterized by having two different fluorophore moieties joined by a linking group comprising at least two positive charges, advantageously used together or in conjunction with a homodimer. The fluorophore moieties of the eterodimer are related in that a first fluorophore moiety has an absorption maximum in solution at less than about 500 nm, usually less than about 450 nm, and generally greater than about 275 nm, usually greater than about 300 nm. The emission maximum for the second fluorophore moiety in solution will generally be greater than 350 nm, usually greater than about 400 nm, and less about 600 nm, usually less than about 550 nm. By contrast, the absorption maximum when intercalated in DNA for the first fluorophore moiety will usually be at least about 375 nm, usually at least about 400 nm, while, more usually at least about 450 nm. The emission maximum for the second fluorophore moiety when intercalated in DNA will generally be at least about 450 nm, more usually at least about 500 nm and usually less than about 750 nm, more usually less than about 700 nm. At least one of the fluorophores will be capable of strongly binding to, usually intercalating, dsDNA.

The second fluorophore moiety will be further characterized, when associated with dsDNA, by having an absorption maximum at least 25 nm greater than the first fluorophore moiety to which it is combined and usually not greater than about 100 nm, more usually not greater than about 75 nm. The second fluorophore will be capable of quenching at least about 80% of the fluorescence which would otherwise be observed from the first fluorophore under the conditions of irradiation, when the subject composition is intercalated into dsDNA. In order to have efficient quenching, there will be overlap between the emission spectrum of the donor and the absorption spectrum of the recipient or second fluorophore. Usually, the ratios of observed fluorescence emission between the higher wave length emitting fluorophore and the lower wave length emitting fluorophore will be at least 1.2, more usually at least about 2, and may be 5 to 1, or more. The Stokes shift between the wavelength of the irradiation, where a narrow wavelength band is employed, particularly a laser, and the fluorescent emission maximum will be at least about 75 nm, more usually at least about 100 nm, preferably greater than about 125 nm. It is advantageous to have a donor chromophore with an extinction coefficient at the excitation wavelength to maximize the effectiveness of light absorption.

While donor fluorophores may have extinction coefficients as low as about 2000, desirably the extinction coefficient will be at least 5000, preferably at least 10,000, and may be 50,000 or more.

The subject heterodimers have novel fluorescent properties. The emission of the absorbing fluorophore is at least about 80%, usually at least about 85% quenched.

In addition, when bound solely to primary binding sites of dsDNA, the emission of the emitting fluorophore is at least about 2 times, usually at least about 7 times, brighter (as great) as the emission maximum of the homodimer of the emitting fluorophores under the same conditions, except for the wavelength of the excitation light. Thus, fluorescence yield can be greatly increased with a weakly absorbing fluorescer.

The subject compositions may comprise two or more fluorophore moieties, where a pair of the fluorophores are related in accordance with the ranges indicated above. The other fluorophores may be the same or different from the pair of fluorophores. If different, the fluorescent properties will usually be governed by the ranges indicated for the pair of fluorophores. Where the fluorophores are different, each fluorophore would have a differential absorption maximum in relation to the next successive fluorophore in accordance with the above-indicated ranges. That is, if there were three different fluorophore moieties, there would be a difference in absorption maxima of at least 25 nm between the first and second and at least 25 nm between the second and third, and so on. Usually, the molecules would not have more than about four different fluorophores, more usually not more than about three different fluorophores. It is not essential that there be any particular order in which the fluorophores are linked, so that they may be linked in a linear manner, from a central linking group having spokes radiating from a center, to a cyclic molecule or other convenient synthetic intermediate, so long as the distance between the fluorophores allows for energy transfer.

The linking group will be characterized by having at least two groups or functionalities that can carry a positive charge or are charged, for example, amino groups or ammonium groups, sulfonium groups, etc., for the most part comprising nitrogen or sulfur as the positive heteroatom. The linking chain may be of a length to allow for simultaneous intercalation to adjacent monomeric units dsDNA, in this case usually providing a length of at least about 10 Ångstroms, usually having at least about 9 atoms, more usually at least about 10 atoms in the chain, and usually not more than about 26, usually not more than about 20 atoms, between fluorescent units, counting the shortest chain where a cyclic linking group is involved.

The linking group will usually be aliphatic or alicyclic, having from 0–8, more usually from 0–6, preferably from about 2–6 heteroatoms in the chain, particularly heteroatoms that would provide for a positive charge. There will normally be at least a total of two positive charges, more usually not more than eight positive charges, more usually not more than about six positive charges on the linking group.

The fluorophoric moieties may be cyclic, polycyclic, particularly polycyclic aromatic having at least two rings, and not more than about six rings, more usually not more than about five rings, where at least two of the rings are fused, usually not more than four of the rings being fused. The aromatic compound may be carbocyclic or heterocyclic, particularly having from 1–3, more usually 1–2 nitrogen atoms as heteroannular atoms. Other heteroannular atoms include oxygen and sulfur (chalcogen).

The rings may be substituted by a wide variety of substituents, which substituents may include alkyl groups of from 1–4 carbon atoms, usually 1–2 carbon atoms, oxy, which includes hydroxy, alkoxy and carboxy, generally of from 1–4 carbon atoms, amino, including mono- and disubstituted amino, particularly mono- and dialkyl amino, of from 0–8, usually 0–6 carbon atoms, thio, particularly alkylthio from 1–4, usually 1–2 carbon atoms, cyano, non-oxo-carbonyl, such as carboxy and derivatives thereof, particularly carboxamide or carboxyalkyl, from 1–8, usually 1–6 carbon atoms, oxo-carbonyl or acyl, generally from 1–4 carbon atoms, halo, particularly of atomic number 9–35, etc.

Fluorophore moieties of particular interest will involve two ring systems, which are joined by a bond or a linking group having one or more ethylenic groups which are in conjugation with the aromatic moieties. Aromatic groups of interest include benzimidazole, benzthiazole, benzoxazole, quinoline and acridine. Illustrative groups include thiazole orange, thiazole blue, ethidium, fluorescein, acridine, phenanthridine, xanthenes, and particularly fluorones.

Couples of fluorophore moieties include thiazole orange and thiazole blue, thiazole orange and ethidium, fluorescein and ethidium, acridine and ethidium, etc. However, acridine has a very low extinction coefficient above 320 nm and is not a donor of choice. Acridine could serve as a donor for thiazole orange or for fluorescein, but would give marginal gains in fluorescence emission.

Compounds can be prepared from alkylene polyamines, where the alkylene groups are from 2–10 usually 2–6 carbon atoms, and haloalkyl- or pseudohaloalkyl substituted fluorescent polycyclic aromatic compounds, to provide for ternary or quaternary amino groups. The amino groups may be quaternized with any convenient alkylation agent, either before or after reaction with the fluorescent compound or may be prepared initially as ternary amines using alkyl amines, where the alkyl group will be of from about 1–6, usually 1–3 carbon atoms.

These compounds find use as labeling agents, where the compounds are used in a process for detection of nucleic acid or as a label which is prepared for labeling a compound to provide a fluorescent signal. By having multiple markers capable of simultaneous detection, many analytical applications are attainable. For example, such applications include fluorescence immunoassay, fluorescence in situ hybridization, and flow cytometric analysis of cell populations, to list a few.

By appropriate combinations of the subject compositions, one can employ dyes which share a common excitation wavelength, exploiting energy transfer to achieve readily resolvable emission wavelengths. In addition, with the dsDNA-dye complex, excitation of the donor leads to greatly enhanced emission from the acceptor, with the donor fluorescence substantially quenched as compared to the appropriate monomer dye in the same environment. Thus, by using combinations of the subject dyes, high-sensitivity multiplex detection of different dsDNA fragments can be achieved.

The subject compositions can find use in separations employing an electrical field, e.g. electrophoresis. In employing the subject compounds, the nucleic acid, usually DNA, and the dye may be brought together in appropriately buffered medium and incubated for sufficient time for the dye to non-covalently bind and intercalate in the nucleic acid. The ratio of dye to double stranded nucleic acid may be varied widely ranging from about one molecule of dye per base pair to as little as one molecule of dye per 400 base pairs, or fewer, usually as few as one molecule of dye per 100 base pairs depending upon the desired degree of sensitivity. Below about 15 bp/dye molecule, the increase in emission upon further addition of dye is not as efficient as above 15 bp/dye. Dye present in excess of one dye for four base pairs or more, may result in total quenching, so that any increase in the amount of dye above a molar ratio of one dye molecule for four base pairs may not be desirable. However, the amount of dye combined with the DNA may be in a ratio of 1 per 2 base pairs or even 1 per 1 base pair or even greater ratios, where quenching is not observed. Generally, the amount of dye will range from about one molecule for 4 to 100 base pairs, usually about 10 to 50 base pairs, for optimum results.

One may combine different samples with different dyes, followed by combining the different samples to be electrically separated. Thus, in the same channel, where an electrophoresis is carried out, one can detect the various bands with light of the same wavelength used for irradiation, by detecting the differences in fluorescent wavelength from the various bands.

The amount of nucleic acid will generally be conventional amounts employed for electrophoresis, generally ranging from about 5 pg/$\mu$l to 5 ng/$\mu$l. Because of the fluorescent efficiency, capillary electrophoresis can be performed efficiently. Various conventional buffers may be employed, such as tris-acetate or tris-borate, generally present in the range of about 1–50 mM, more usually in the range of about 1–20 mM, to provide a pH in the range of about 5–10, more usually about 7–9. Also, a metal ion chelator may be present in a minor amount, generally from about 0.05–0.5 mM. Conveniently, EDTA may be employed.

The dye and nucleic acid may be incubated, usually for at least about 5 minutes and not more than about 2 hours, where complex formation will normally be complete in less than about 1 hour, usually in about 30 min., at room temperature. The incubated solution may be used directly or further diluted, as appropriate, prior to application to the gel.

The electrophoresis may be performed in any convenient and conventional manner, where the bands may now be detected by fluorescence of the non-covalently bound and intercalated dye. The electrophoresis ensures that unbound dye is removed from the region of the bands and the dye is found to be retained in the nucleic acid, so that individual bands may readily be detected by fluorescence scanning.

Instead of incubating the nucleic acid with the dye prior to applying the nucleic acid to the gel, one may apply the dye after having carried out the separation. Since the intercalated dye will have a substantially different absorption-emission range (and much enhanced fluorescence intensity) from the unintercalated dye, one can readily detect the intercalated dye, even in the presence of significant amounts of the non-intercalated dye.

Any conventional detection system may be employed for detecting the individual bands. Depending on the particular dye employed, the excitation light will be chosen to be within a major absorption band of the absorbing dye.

Of particular interest is the use of a confocal laser scanning fluorescence imaging system. A system which has been found to be convenient employs a long-pass dichroic beam splitter to reflect the laser beam down through a microscope objective and onto the sample. The fluorescence emission is collected by the objective and passed through the bea,m splitter to a photodetector. The fluorescence emission is then passed through a spatial filter to effect confocal detection in a long-pass or band-pass color or interference filter before reaching a photomultiplier tube. An appropriate servomotor-driven XY translation stage is employed with a 2.5 $\mu$m resolution to translate the gel past the laser beam at a convenient speed, nearly about 1–5 cm/sec. A microcomputer may be employed to control the XY translation stage and to acquire and display images. The fluorescence images may then be pseudo-colored and coded to represent different intensity levels and contrast stretched with a histogram equalization method to enhance the images. To quantitate the image data, the image columns that enclose the nucleic acid bands may be extracted and integrated.

The nucleic acid may be readily isolated free of the intercalated fluorescent dye for further use. One may use the Genecleans kit for recovery of 50% or better of the nucleic acid. By combining the intercalated dye containing nucleic acid with Glassmilk in an aqueous solution of alkali metal iodide, e.g. 1–10 $\mu$g nucleic acid (1–5 $\mu$g/ml nucleic acid) and about 1–10 $\mu$g/ml of Glassmilk, incubating with agitation for about 5–60 mins. followed by centrifugation, the resulting pellet is isolated. After resuspending the pellet in an appropriate ethanolic buffered aqueous solution (e.g. 1:1) followed by centrifugation and repeating this washing procedure, the nucleic acid is obtained substantially free of the fluorescent dye.

By virtue of the use of the subject intercalating fluorescent dyes in the electrophoresis, greatly enhanced sensitivities are achieved due to the much higher level of fluorescence intensity which is obtained. Sizes and amounts of DNA fragments in mixtures of unknown composition can be determined with a total amount of material ranging from 100 pg to 1 ng depending on the complexity of the mixture and the size range of the fragments. Thus, the subject method can find application in the detection of nucleic acid of less than about 5 ng, particularly less than about 1 ng, frequently less than about 100 pg, even less than about 50 pg.

Instead of employing the subject dyes for detection of nucleic acid bands in electrophoresis, compositions comprising dsDNA and the subject dyes at substantial saturation may be employed, where the dsDNA is joined to an entity for binding to another entity, either covalently or non-covalently. The entities will be either referred to as specific binding pairs, since the entities will have specific affinity for a complementary entity, as compared to diverse other types of molecules, or covalently binding functionalities for reacting with other molecules, such as polypeptides or saccharides.

The specific binding pairs may involve a wide variety of molecules, which are arbitrarily called ligands and receptors. For the subject invention, the ligands and receptors may include a wide variety of proteins, such as antibodies, specific binding proteins, such as surface membrane protein receptors, lectins, blood proteins, and the like, carbohydrates, small organic molecules, both naturally occurring and synthetic to which proteins specifically bind, either naturally occurring protein receptors or antibodies, nucleic acids which may hybridize or specifically bind to an homologous or partially homologous sequence usually having at least about 30% complementarity, preferably at least about 50% complementarity over the complementary region, and the like. In effect, any two molecules which have a specific binding affinity may be employed, so that the label may be used for detection of the presence of the complementary member. The desired specificity may be varied widely, depending upon the particular nature of the molecules to be detected, the information desired about the nature of the sample, or the like.

The labels may be used for detecting any of a wide variety of molecules in a wide variety of samples, which includes physiological samples, e.g. blood, plasma, urine, spinal fluid, saliva, feces, mucus, etc., waste samples, from processing, garbage, soil, water, etc., contaminants in products, such as food, drugs, etc.

Depending upon the fluorescence intensity one desires, one can vary the length of the dsDNA and the level of non-covalent binding and intercalation to increase the fluorescence intensity per molecule. Usually, there will be at least about 16 base pairs, more usually at least 20 base pairs, and one may have dsDNA of at least about 1 kbp or even 2 kbp or more. The particular length of the dsDNA is not critical to this invention and may be varied in accordance with the fluorescence intensity desired per molecule, purpose of the label, convenience, and the like. It is found that with some dyes, e.g. ethidium-acridine heterodimer, there is an increase in fluorescence intensity by having A-T pairs. Thus, one may provide for a poly A-T.poly A-T dimer to be used as the label. However, if one wishes to further increase the stability of the dsDNA, beyond that which the intercalating dimer provides, one can use a combination of AT and GC pairs or a poly G-C.poly G-C dsDNA. Alternatively, one may use any source of random DNA, such as calf thymus DNA, E. coli DNA, etc.

The dsDNA should provide for means for binding to another molecule. This can be achieved in a wide variety of ways, depending upon the manner in which the label is to be employed. For example, the dsDNA may include biotin conjugated nucleotides, one or more biotins, where the biotin will bind to avidin or streptavidin (hereafter both will be referred to as "avidin"). The biotins may vary from one biotin per nucleotide to 0.1% of the nucleotides depending on the nature of the procedures, conditions, etc. Alteratively, any molecule may be employed, particularly a small organic molecule (less than about 2 kdal) which is unlikely to be encountered in the sample of interest, where the small organic molecule has a specific receptor or antibody, particularly monoclonal antibody, to which it specifically binds. Thus, thyroxine, corticosteroids, estrogens, retinoic acid, mannose and the like may be used with proteins which bind specifically to such molecules. Alternatively, synthetic molecules may be employed for which antibodies have been produced, such as 2,4-dinitrophenyl, barbiturate, phosphatidylcholine, etc. These molecules may be included during synthesis of the DNA by being linked to an internal or terminal nucleotide, where the DNA is synthesized in accordance with conventional automatic procedures, or may be added after synthesis of the DNA by linking to either available hydroxyl or amino groups.

The binding entity may be an active functionality for covalently bonding to a molecule having a functionality capable of forming a stable covalent link, such as amino, hydroxyl, thio, carboxyl, activated olefin or aryl, or the like where the functionality is other than a naturally occurring functionality of the nucleotide. The label may be modified with an activated olefin, such as maleyl, for reaction with a thiol group, a carboxyl for reaction with an amine, or the like. In this manner, many different types of molecules may be fluorescently labeled for use in diagnostics, both competitive assays and non-competitive assays, histology, cytology, separations e.g. electrophoresis, HPLC, FACS, and the like.

The strands of DNA may take various structures. In many situations, the dsDNA may comprise two strands, where the strands may be completely or only partially overlapping, where the ends may extend in the 5' and/or 3' directions, so that one strand may be substantially longer than the other strand, where the other strand may bind either 5' proximal, 3' proximal or centrally. Alternatively, the two strands may overlap to provide for staggered ends, where the single stranded portions of the DNA may then be used to bind to complementary sequences. Alternatively, one may provide a single strand with an inverted repeat, so that the strand loops back on itself to provide the double stranded portion. The hairpin structure may be used solely for labeling, or a single stranded portion of the hairpin may be employed for hybridizing to a complementary sequence. The hybridizing single stranded portion may be an extension at either the 5' or 3' end to provide for a staggered terminus or may be present in the loop of the hairpin.

The subject labels may be used in a wide variety of environments and contexts to provide for high levels of fluorescence intensity without interference from the molecules to which the labels bind, either directly or indirectly, the media employed, the conditions employed, and the like. Thus, the subject labels may be employed in specific binding pair assays, where the label may be readily linked to another molecule through a specific binding pair combination. For example, in diagnostic assays, one may combine an avidin conjugated antibody, where the antibody binds to a molecule of interest, to a biotin labeled DNA dye composition to provide for fluorescent labeled antibody.

Alternatively, the antibody may be labeled with biotin, so that avidin may act as a bridge between the biotin labeled antibody and the biotin labeled DNA dye composition. In this way, the fluorescent label may be added after combining the sample with a complementary specific binding pair member and carrying out the assay, followed by addition of label and removal of any nonspecifically bound label.

Where a single stranded DNA sequence is provided as part of the label, this can be used for hybridizing to complementary DNA or RNA sequences. The presence of the non-covalently bound and intercalated dye greatly enhances the stability of the dsDNA. Thus, one can introduce the subject labels into a denaturation medium under conditions where the non-covalently bound and intercalated dsDNA will be stable, while the sample DNA may be denatured to provide for single strands. Where single stranded DNA or RNA is present, there will be no need for providing for denaturation conditions. Therefore, the subject molecules may be used as probes to identify DNA sequences under a wide variety of conditions, including electrophoresis, polymerase chain reactions, where the single stranded sequence may serve as a primer, in Southern blotting, Northern blotting and the like.

Instead of having non-covalent complexes between the non-nucleic acid specific binding pair member and the DNA dye aggregate, one can provide for covalent bonding. Thus, by providing for activated groups such as carboxy, diazo, azido, activated ethylene, or the like, the fluorescent moiety may be readily linked to other molecules, such as proteins, sugars, lipids, or the like by employing conventional linking groups resulting in amides, amines, diazo, esters, thioethers, or insertion into a carbon-hydrogen bond or addition to a double bond, and the like. For example, one may introduce a thiol group at either the 3' or 5' terminus of a synthetic oligonucleotide, synthesize the complementary strand and form a non-covalently bound and intercalated dye complex. The thiol group on the DNA can then be reacted with a maleimide modified protein, e.g. an antibody. One can add an acylmethylazide and upon phototypes produce a nitrene which would randomly insert or add to a double bond. Other techniques may follow conventional procedures found in the literature.

The subject DNA dye composition may also be used in situations where one wishes to transfer energy or receive energy from another molecule. Thus, the subject compositions may be used with other fluorescent dye substituted molecules, e.g. dye intercalated DNA molecules, for receipt or transfer of excitation energy, or with other fluorescent molecules, so as to extend the shift between the excitation light and the emission light. This technique may be used in diagnostic assays, or where one wishes to determine the spatial relationship between two entities, e.g. epitopes, surface membrane receptors, etc.

One may also use the subject labels in a fluorescence activated cell sorter to provide for greatly enhanced sensitivity as a result of the substantially increased fluorescence intensity. Again, one may use ligands for surface membrane receptor proteins, sugars for lectins, antibodies for epitopes present on the surface of the cell, or the like, where the subject labels may be bound covalently or non-covalently, to the molecule which binds to the cell component.

With the subject compositions one can also detect proteins to transcriptional initiation elements, e.g. promoters, operators, enhancers, etc. By having labeled dsDNA, according to the subject invention, mixed with labeled proteins, labeled with a fluorescent molecule emitting at a different wavelength from the non-covalently bound and intercalated fluorescer, or other appropriate label, one can determine the presence of transcription factors and cofactors. For example, one can gel electrophorese the mixture and identify the presence of the protein bound to DNA by virtue of the double labelling and band shift.

One may also use the subject fluorescent non-covalently bound and intercalated DNA for in situ hybridization studies, intermolecular transfer of fluorescent molecules from one doubly stranded nucleic acid molecule to another, e.g. for transferring fluorescent dye without the fluorescer being-transferred to the medium. This may find use in making chromosomes with triplex formation, in transferring to nucleic acid in a gel or on a membrane, etc. The fluorescer intercalated DNA may be bound to a particle, e.g. magnetic, to be removed after use as a transfer agent.

The subject compounds may be used with advantage with a confocal fluorescence imaging system, where less than 100 pg of DNA can be detected with some dyes while with other combinations, less than about 5 pg of DNA can be detected. In histology and cytology, the subject fluorescent labels provide for high-sensitivity in detecting target epitopes, particularly at low levels.

Besides using the dyes individually, the dyes may be used in combination for a wide variety of applications, where one wishes to obtain at least two bits of information concerning the sample or composition of interest. Since the intercalated dyes have different absorption and emission spectra from the non-intercalated dyes, one can detect the presence of the two dimeric compounds when intercalated into DNA, while in the absence of DNA, there would be substantial overlap, so that only poor discrimination would be obtained. Furthermore, one need not use the heterodimers of the subject invention solely, since the heterodimers may be used with homodimers, where the heterodimer and homodimer have the same absorbing fluorophore or different absorbing fluorophore excited by a common wavelength range, but obviously differing in the emitting fluorophore. Thus, ethidium dimer, thiazole orange dimer, thiazole blue dimer, oxazole yellow dimer, and the like may be used in conjunction with heterodimers, where usually the same absorbing fluorophore is present, although in many instances, a different absorbing fluorophore will suffice, where the two absorbing fluorophores have overlapping absorption peaks.

By using the combinations employing the subject dyes, detection of two different events may be obtained in a number of different environments. of particular interest is flow cytometry, where a single exciting light may be used and the fluorescence determined as to two or more events. The events may involve binding events to two different epitopes of the same or different protein, where a single protein may be involved or an aggregation of proteins, as is present in viruses and cells or significant fragments thereof. In this way, one may select for particles such as cells, by virtue of the presence of two different markers, using a single exciting laser. Similarly, in histology and cytology, one may determine the presence of different proteins which may be present on the same or different cells or present extracellularly. As appropriate, one may inject the dyes bound to a specific binding molecule into a laboratory animal to follow the migration of different molecules or cells, where one is interested in the presence of the two different targets at a particular site. Numerous other applications, where single excitation light is desired, while a plurality of different information values is desired concurrently, have been generally described in literature and will be further developed as the subject invention becomes available.

For many applications, a plurality of fluorescent molecules will be desirable. Kits can be provided where the fluorescent molecules in the kit are characterized by having absorption maxima within about 25 nm, so that excitation light of a relatively narrow bandwidth may be used, generally of not more than about 30 nm, usually of not more than about 20 nm. The absorbing fluorophore may be the same or different.

The kit will have two or more fluorescent multimers, each having from two to four, usually two to three, fluorophores, wherein at least one of the fluorophores is able to bind, usually intercalate, into dsDNA. At least one of the multimers will be a heteromultimer being characterized by having a Stokes shift of at least about 25 nm, capable of binding dsDNA at a ratio of at least one dye per 200 bp dsDUA without diminishing the fluorescence as compared to one fluorophore per dsDNA molecule on a per dye basis, and the fluorophores absorb and emit at different wavelengths, when bound or unbound to dsDNA. Besides the at least one heteromultimer, the other multimers may be homomultimers, of particular interest are homo- and heterodimers and heterotrimers.

The following examples are offered by way illustration and not by way limitation.

EXPERIMENTAL
SYNTHESIS OF DYES

Materials and Methods. The starting materials including 3-methyl-benzothiazole-2-thione, lepidine, 3,8-diamino-9-phenylphenanthridine, fluorescein isothiocyanate isomer I, diethylenetriamine, tetramethyl-1,3-diaminopropane, 1,3-diaminopropane, anhydrous HBr/acetic acid were purchased from Aldrich and used without further purification. Anhydrous methanol, triethylamine, and pyridine were distilled from sodium and stored under nitrogen. Anhydrous nitrobenzene was freshly distilled from $P_2O_5$. All anhydrous reactions were run in oven dried glassware under a nitrogen atmosphere. Reactions were monitored by TLC (Merck $A_{254}$) under short and long wavelength UV light. Flash chromatography was performed on 220–440 mesh silica gel 60 from Fluka.

Intermediate products which gave single spots on TLC were identified by their IH-NMR spectra measured with an AMX-300 instrument. UV/VIS absorption spectra were measured with a Perkin Elmer Lambda 6 spectrophotometer and fluorescence emission spectra with a Perkin Elmer MFP 44B spectrofluorometer.

Synthesis of Heterodimers. As outlined in FIG. 1, the N-3-iodopropyl derivatized lepidine (1), reacted in under 15 minutes with the N-methyl 2-methylthio benzothiazole (2) or N-methyl 2-(N'-phenyl, N'-acetyl, 3-azopropylidene benzothiazole (4) to yield the iodopropyl thiazole orange intermediate (3), or iodopropyl thiazole blue intermediate (5) (TB), in good yields following the method of Brooker et al. ((1942) JACS 64:199–210; (1941) JACS 63:3192–3203). Compound (1) was produced in high yield by alkylation of lepidine with 5 equivalents of 1,3-diiodopropane in refluxing dioxane, while compound (2) was formed quantitatively when 3 equivalents of iodomethane were reacted with 3-methylbenzothiazole-2-thione in refluxing 200 proof ethanol and precipitated with ether. Compound (2) was also used as an intermediate in the synthesis of (3) (Brooker et al., supra).

FIG. 1. Synthesis of thiazole monomer intermediates. a) Suspend in absolute EtOH, add 1 equivalent TEA, stir at room temperature for 15 minutes, precipitate with ether, recrystallize from acetone/ether; yield 80% 3, 60% 5.

To synthesize the thiazole orange-thiazole blue heterodimer, the iodopropyl thiazole orange derivative (4) was reacted with excess tetramethyl-1,3-diaminopropane (Scheme 2) to produce the intermediate tetramethyldiaminopropyl thiazole orange derivative (6). Compound (6) (TO6), after purification by recrystallization, reacted with the thiazole blue derivative (5) to produce a good yield of the thiazole orange linked thiazole blue heterodimer TOTAB (7). Dimerization of (4) (as described in Rye et al., *Nucleic Acids Res.* (1992) 20:2803–2812) was used to synthesize nearly quantitatively the homodimer TOTO (8) employing 0.5 equivalents of tetramethyl-1,3-diaminopropane.

Figure 2:
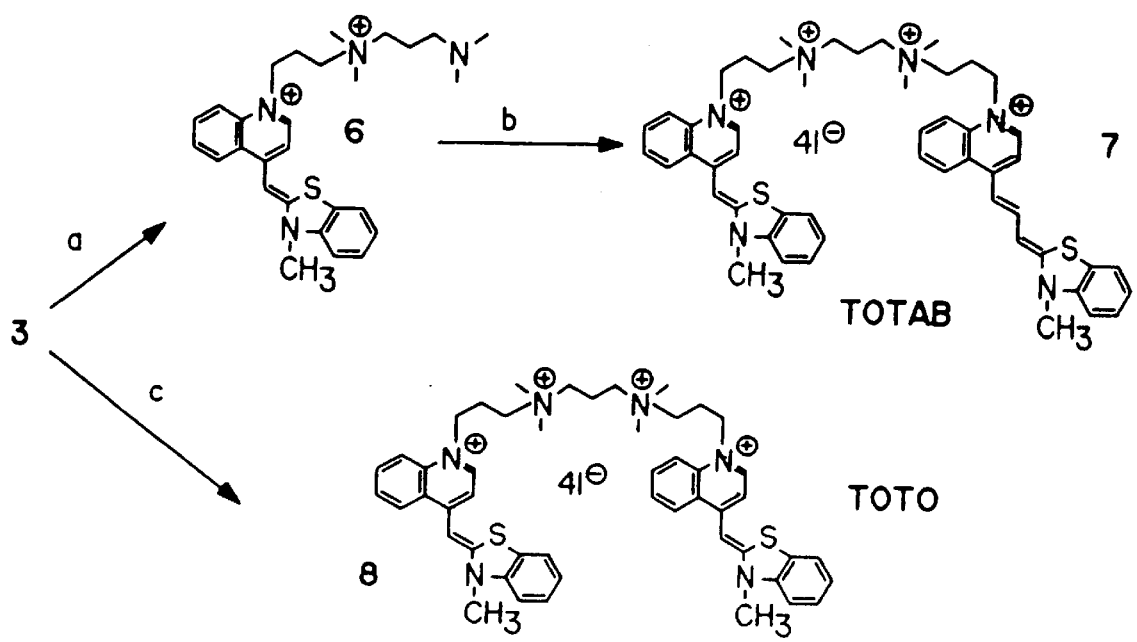
FIG. 2 is a synthetic scheme for the synthesis of thiazole dimers (TOTO and TOTAB)

FIG. 2. Synthesis of the thiazole dimers. a) Suspend in anhydrous MeOH, add 6 equivalents tetramethyl-1,3-propanediamine, reflux 6 hours, precipitate acetone/ether, recrystallize MeOH:$CH_2Cl_2$ (1:10)/acetone; yield 80% 6. b) Suspend in anhydrous MeOH, add 1 equivalent (5), reflux 10 hours, precipitate with ether, triturate solid with MeOH:$CH_2Cl_2$ (1:10), flash column EtOAc:AcOH:$H_2O$ (1:2:2); yield 70% 7. c) Suspend in anhydrous MeOH, add 0.5 equivalents tetramethyl-1,3-propanediamine, reflux 18 hours, precipitate with acetone, titurate solid with MeOH:$CH_2Cl_2$ (1:10), recrystallize from MeOH/acetone; yield 95% 8.

Figure 3:
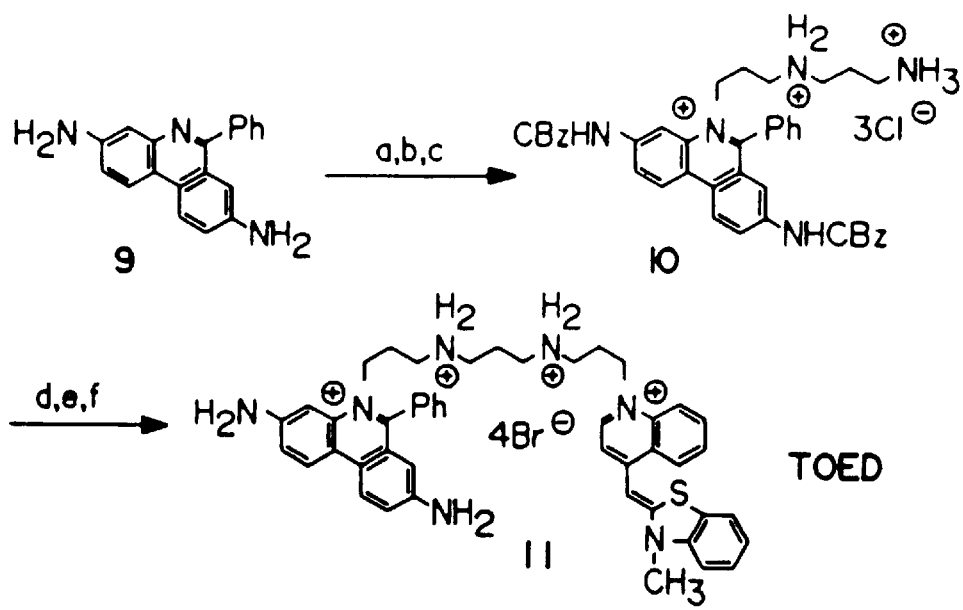
FIG. 3 is a synthetic scheme for the synthesis of thiazole-ethidium dimer (TOED)

The thiazole orange-ethidium heterodimer was obtained as outlined in FIG. 3 from 3,8-diamino-9-phenylphenanthridine (9) via intermediate (10). In general, the synthesis of the thiazole orange-ethidium heterodimer (11) followed the method of Gaugain et al. ((1978) *Biochemistry* 17:5071–5078) except that carbobenzyloxy groups were used to protect the amino substituents in place of acetate or carboethoxy groups. After coupling (10) with the thiazole derivative (3), the crude solid dicarbobenzyloxy-protected intermediate was deprotected (anhydrous HBr/AcOH) to produce a low unoptimized yield of the desired thiazole orange-ethidium heterodimer TOED (11) and substantial amounts of undesired byproducts. Employing tetramethyldiaminopropane in place of diaminopropane as a linker in the synthesis of thiazole orange-ethidium heterodimer gave an improved yield of the analogue, TOED-2, with a quaternized methylenediamine linker. The fluorescein-ethidium heterodimer was synthesized as described in FIG. 4.

FIG. 3. Synthesis of the thiazole-ethidium heterodimer. a) Suspend in anhydrous pyridine, add dropwise 2.2 equivalents carbobenzyloxychloride at 0° C., stir to room temperature over 12 hours, precipitate with ether/pet ether, suspend solid in $CH_2Cl_2$ and wash with 10% $NaHCO_3$, dry organic layer, concentrate, flash column MeOH:$CH_2Cl_2$ (1:50). b) Suspend in anhydrous nitrobenzene, add 5 equivalents 1,3-diiodopropane, heat at 160° C. for 4 hours, precipitate with ether, flash column MeOH:$CH_2Cl_2$ (1:10). c) Suspend in anhydrous MeOH, add 10 equivalents 1,3-diaminopropane, reflux 7 hours, precipitate $H_2O$, suspend EtOH and acidify with concentrated HCl, precipitate with ether, flash column EtOAc:AcOH:$H_2O$ (6:3:2); yield 22% (10) from (9). d) Suspend in MeOH, add 3 equivalents 1N NaOH, precipitate/wash solid with $H_2O$, dry solid at 60° C. in oven. e) Suspend in anhydrous MeOH, add 0.7 equivalents 3, reflux 10 hours, precipitate ether/pet ether; used without further purification. f) Suspend in anhydrous HBr/AcOH, stir at room temperature for 1 hour, concentrate, suspend in $CH_2Cl_2$ precipitate with TEA/ether, flash column EtOAc:AcOH:$H_2O$ (6:3:2).

Figure 4:
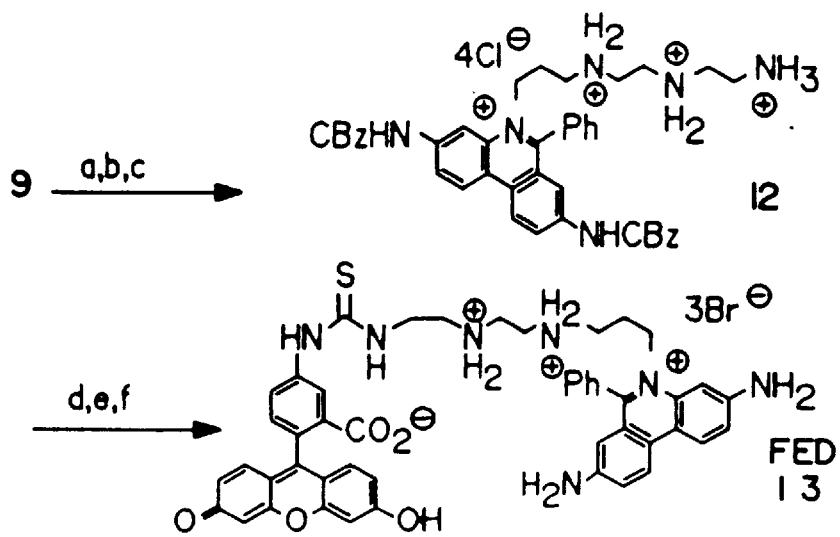
FIG. 4 is a synthetic scheme for the synthesis of fluorescein-ethidium heterodimer (FED).

FIG. 4. Synthesis of the fluorescein-ethidium heterodimer. Steps (a) and (b) are performed exactly as described for steps a and b in Scheme 3. c) Suspend in anhydrous MeOH, add 10 equivalents of diethylenetriamine, reflux 7 hours, precipitate $H_2O$, suspend in EtOH and acidify with concentrated HCl, precipitate with ether, flash column EtOAc:AcOH:$H_2O$ (6:3:2); yield 28% (12) from (9). d) Suspend in MeOH, add 4 equivalents 1N NaOH, precipitate/wash solid with $H_2O$, dry solid at 60° C. in oven. e) Suspend in anhydrous MeOH, add 1.1 equivalents of FITC, stir at room temperature 2 hours, acidify with concentrated HCl, precipitate with ether, solid used without further purification. f) Suspend in anhydrous HBr/AcOH, stir at room temperature for 1 hour, concentrate, suspend in $CH_2Cl_2$, precipitate with TEA/ether, flash column EtOAc:AcOH:$H_2O$ (7:3:2).

The linked structure of the dyes, TOTAB (7), TOED (11) and FED (13), was established by the presence of both monomer UV/visible absorptions in the chromatographically pure dimers which were shown to contain none of the monomeric starting materials thiazole orange (6), thiazole blue (5), ethidium derivatives (10) or (12), or fluorescein isothiocyanate by TLC (in 1:1 v/v MeOH:CH$_2$Cl$_2$ and EtOAc:AcOH:H$_2$O 1:2:2, by volume). The visible absorption maxima in MeOH at 507 nm and 633 nm exhibited by TOTAB, and the 294 nm and 486 nm absorptions of FED, clearly indicated the presence of linked chromophores in the dyes (See Table 1).

TABLE 1

| Dye | MeOH | | TAE Buffer | | TAE Buffer/DNA | |
|---|---|---|---|---|---|---|
|  | λ max | ε | λ max | ε | λ max | ε |
| TOTAB | 302 | 22 000 | 302 | 15 000 |  |  |
| 7 | 505 | 77 600 | 506 | 57 100 | 514 | 60 800 |
|  | 633 | 101 000 | 644 | 55 800 | 646 | 46 600 |
| TOED | 295 | 62 000 | 288 | 53 600 |  |  |
| 11 | 476 | 50 500 | 472 | 54 100 | 472 | sh |
|  | 507 | 56 400 | 507 | sh | 515 | 57 500 |
| TB | 304 | 12 800 |  |  |  |  |
| 5 | 633 | 160 500 | 304 | 10 100 |  |  |
|  | (505, ε = 2 600) |  | 628 | 75 300 | 639 | 70 200 |
| TO | 290 | 13 200 | 288 | 10 500 |  |  |
| 6 | 507 | 76 000 | 507 | 64 300 | 515 | 61 700 |
| FED | 294 | 72 000 | 288 | 68 800 |  |  |
| 13 | 486 | 13 200 | 495 | 72 300 | 492 | 48 600 |
| FITC | 280 | 23 200 | 280 | 24 200 |  |  |
|  | 456 | 2 800 | 492 | 72 000 | 492 | 72 000 |
| Ethidium | 294 | 48 800 | 284 | 44 600 |  |  |
| Bromide | 520 | 5 500 | 475 | 5 500 | 516 | 4 200 |

Absorption spectra of equal concentrations of the monoters were added to closely approximate the spectra of an equal concentration of the linked dimers. Comparison of the absorption spectra of thiazole orange (6) and thiazole blue monomer (5) established that less than 3% of the absorption at 505 nm of the TOTAB dimer was due to the thiazole blue portion of the dimer. Thus, the extinction coefficient of the thiazole orange monomer (6) plus the extinction coefficient of the thiazole blue monomer (5) at 505 nm was assigned to the 505 nm absorption of the TOTAB dimer (ε=77 600 M$^{-1}$cm$^{-1}$) and used in all subsequent TOTAB concentration determinations. For the TOED dimer, addition of the separate spectra taken of equal concentrations of ethidium bromide and (6) closely approximated that of an equal concentration of the dimer in the UV region of the spectrum, and was used to determine an extinction coefficient (ε=62 000 M$^{-1}$cm$^{-1}$) for absorption at 295 nm for the TOED dimer. Calculation of the extinction coefficients at the UV and visible absorption maxima of FED (13) were complicated by the high sensitivity of the visible absorption spectrum of the fluorescein chromophore to solvent. The ultraviolet absorption spectrum of FED in methanol and in TAE was closely approximated by the sum of the absorption spectra of equal concentrations of fluorescein isothiocyanate and ethidium bromide. A pronounced tendency of the dyes to retain salts produced during the various stages of the syntheses precluded easy direct measurement of their extinction coefficients based on dry weight.

SPECTRA OF dsDNA-HETERODIMER DYE COMPLEXES

Fluorescence spectra of TOTAB, TOED and FED bound to calf thymus dsDNA at 100 bp:dye, with excitation at 488 nm, were determined. Fluorescence spectra of the free dimers were uninformative as the emissions overlapped to produce a broad fluorescence centered at 660 nm for TOTAB and 630 nm for TOED. The large bathochromic shift for the thiazole orange portion of each dimer upon binding to DNA produced two emission maxima in the spectra of the bound dyes. Under these conditions, TOTAB fluoresced maximally at 532 nm and 662 nm corresponding to thiazole orange and thiazole blue emissions. TOED fluoresced maximally at 532 nm and 610 nm corresponding to thiazole orange and ethidium emissions. Tight binding of the dyes to DNA was indicated by the 384 fold increase in the long wavelength fluorescence emission of TOTAB, and the 227 fold increase in the long wavelength fluorescence emission of TOED upon binding DNA relative to the fluorescence of the dyes free in solution. The strong fluorescence enhancement of bound versus free TOTAB and TOED dyes indicated tight binding of both chromophores to the DNA. The lack of a blue shift in the thiazole blue portion of TOTAB upon binding DNA (emission at 660 nm free versus 662 nm bound) suggested that this portion of the molecule may in fact be bound in a non-intercalative mode in the minor grove of the DNA exposed at least in part to the external aqueous environment.

From comparison of the absorption spectra of bound dyes to the fluorescence emission of the bound dyes upon irradiation at 488 nm it was evident that energy transfer occurred between donor and acceptor chromophores in both dyes. The observed enhancement of the thiazole blue portion of the TOTAB emission at 662 nm, relative to the 532 nm emission produced by 488 nm excitation of the thiazole orange portion of the dye, was the clear result of energy transfer given the absorption profile of the bound dye. Similarly, the visible absorption profile of TOED bound to DNA was dominated by the thiazole orange absorption at 488 nm (ε donor:ε acceptor=14:1), yet energy transfer upon excitation at 488 nm resulted in a larger ethidium emission at 610 nm then the thiazole orange emission at 532 nm. The observation of highly efficient energy transfer at a DNA bp:dye ratio of 100:1, provides independent evidence that the donor and acceptor chromophores in TOTAB and TOED are linked to each other. Plots of the emission spectra of the unlinked thiazole orange monomer TO6 (compound 6) bound to DNA when compared at the same concentration of TOTAB and TOED bound to DNA demonstrated that the thiazole orange emission of the bound heterodimers was more than 90% quenched at well below saturation of binding sites (100 bp:dye) on the DNA. Similarly, a comparison of the emission spectra of FED and the same concentration of fluorescein isothiocyanate demonstrates that greater than 90% quenching of the fluorescein emission occurrs in the bound dimer. A comparison of the fluorescence emissions of the heterodimers to ethidium dimer bound to DNA was also examined: the TOTAB dimer fluoresced over 9 times as brightly as ethidium dimer in solution at its emission maximum while the TOED dimer fluoresced 8 times as brightly. Based on the ratio of 610 nm emission of ethidium fluorescence in TOED versus the 610 nm emission of the two ethidium chromophores in the ethidium dimer (taking into account the extinction coefficient ratio of ethidium to ethidium dimer; 5500:8900), a 15-fold fluorescence enhancement of the ethidium chromophore emission in the TOED dimer, bound to DNA at 100 bp:dye, was calculated. This result exemplifies convincingly the ability of energy transfer to increase fluorescence yield of a weakly absorbing chromophore.

Titrations of calf thymus dsDNA with TOTAB and TOED, monitored at the acceptor emission maxima or plotted as the ratio of acceptor/donor emission maxima, led to a variety of significant observations. As sites on the DNA become saturated with dye, the emissions of both donor and acceptor chromophore per mole of added dye become increasingly quenched particularly the donor emissions. Titrations of calf thymus DNA monitored by the acceptor chromophore emissions and normalized per mole of added dye indicate an approximately linear relationship of fluorescence per mole of added dye from 100 to 20 bp per dye, indicating that in solution the binding of the dyes does not show strong sequence specificity. Titration was performed by adding concentrated aliquots of stock dilutions of the dye to calf thymus DNA ($c=5\times10^{-6}$ M bp) in 0.5 mL of 4 mM TAE and incubating the mixture for 15 minutes prior to recording each spectrum. The two sets of titration data obtained were normalized relative to each other by recording the emission spectra of the two dyes bound to calf thymus DNA at 100 bp dye under identical conditions. As sites on the DNA become saturated beyond 20 bp:dye, the amount of emission per mole of added dye diminishes rapidly. Secondary site binding is a common property of intercalator dyes as primary sites become saturated with dye (Gaugain et al. (1978) *Biochemistry* 17:5078–5088). Judging from the rapid drop in emission as primary intercalative sites on the DNA are saturated, it appears that for both dyes, binding to secondary non-fluorescent sites caused external quenching of the primary site bound dye.

Analysis of the ratio of emissions of the donor and acceptor chromophores as a function of the ratio of bp DNA to dye (see above for conditions) showed that the amount of quenching of the thiazole orange donor emission of the dyes compared to the quenching of acceptor emission is strongly dependent on the fractional saturation of binding sites on the DNA. As the percentage of neighboring acceptor chromophores increases, the thiazole orange donor emission becomes increasingly quenched. At saturating levels of dye, the thiazole orange emission at 532 is nearly quenched for both TOTAB and TOED bound to DNA. Thus, for the titration employing TOTAB at 3 bp:dye, a maximal ratio of acceptor:donor fluorescence of 17:1 is reached, while in the titration with TOED a maximal ratio of acceptor:donor fluorescence of 39.5:1 is attained. For both TOTAB and TOED dyes bound to DNA, in the presence of excess dye (at 0.5 bp DNA:dye) emissions of both donor and acceptor are almost completely quenched.

The spectrum of the fluorescein-ethidium heterodimer (FED, compound 13) was determined. Comparison on an equimolar basis of the fluorescence emission spectra of FED versus that of ethidium homodimer, both in presence of calf thymus DNA at 100 bp DNA:dye, showed that above 620 nm FED emits over 7 times more fluorescence than ethidium homodimer.

DETECTION OF dsDNA ON GELS

Materials and Methods, Electrophoretic separations and detection of dsDNA-dye complexes are performed by following the procedures described by Rye et al., supra. Electrophoresis is performed in a Mini-Protean II apparatus (BioRad, Richmond, Calif.) in 1 mm thick, vertical 0.9% agarose gels run at 10 V/cm in 40 mM Tris-acetate-EDTA (TAE), pH 8.2. Gels were pre-electro-phoresed for 1 hour prior to sample loading. Working stocks of dyes ($c=1\times10^{-7}$M) are freshly prepared from concentrated stock dyes ($c=1\times10^{-4}$M in MeOH or DMSO), before each experiment by dilution into 4 mM TAE, pH 8.2. The known instability of the cyanine and ethidium dyes in basic buffers (Rye et al., supra) mandates that working stocks in TAE be freshly prepared. For a typical 1 ng λ DNA/HindIII DNA load, concentrated DNA (2 µl of 10 ng/µl DNA) is added to the dye in 4 mM TAE pH 8.2. The dye is diluted from the working stock to give the correct DNA bp:dye ratio upon addition of the DNA in a final volume of 75 µl of a 0.27 ng/µl DNA ($4.19\times10^{-7}$ M bp) plus dye ($4.19\times10^{-8}$ M dye for 10 bp:dye) mixture which is subsequently incubated in the dark for 30 minutes. After the 30 minute incubation period, 25 µl of 15% aqueous Ficoll solution is added to give 100 µl of a 0.2 ng/µl DNA-dye mixture containing 5% Ficoll. A 5 µl (1 ng DNA load) sample of this mixture is loaded on the agarose gel and electrophoresed in the dark for 1 hr. The gel is subsequently scanned with a confocal imaging system (Rye et al., surra). The data are analyzed as previously described in Rye et al., supra.

Results. Initial electrophoresis experiments with a λ DNA/HindIII ladder showed that the heterodimeric dye-DNA complexes, in particular, the cyanine dimers TOTO and TOTAB dye-DNA complexes, gave variable results due to a tendency of the complexes to streak and precipitate in the wells of the gel. To produce consistent results, for TOTAB, addition of 100 mM NaCl to the dye solution in 4 mM TAE prior to incubation with DNA resulted in complete elimination of the streaking and precipitation problems. The use of 40 mM TAE incubation buffer had been previously observed to improve band patterns in studies with oxazole yellow dimer (Rye et al., supra). Further studies showed that band sharpness and signal intensity were not improved at <50 mM NaCl, but were optimal at 80 to 100 mM salt. Signal intensity of the bands dropped at >150 mM NaCl in 4 mM TAE or 40 mM TAE in the incubation mixture, likely due to a lower binding constant of the dye for DNA at the higher salt concentrations. For all dyes studied, addition of 50–100 mM NaCl to 4 mM TAE buffer in the incubation mixture produced consistent results and was subsequently employed in all experiments.

A comparison of the signal intensities of dsDNA complexes of TOTAB, TOED and ethidium dimer bound to the same amount of λ DNA/HindIII DNA all at a 5 bp:dye ratio and run on the same gel, showed that TOTAB was 4–5 times as bright as ethidium dimer, but TOED was found to be only slightly brighter than ethidium dimer. The modest increase in sensitivity of DNA detection with TOED was due to the rapid loss of TOED from the DNA during electrophoresis. In contrast, TOED-2 formed a much more stable complex with DNA and allowed two-fold higher sensitivity of DNA detection than is possible with ethidium homodimes. For TOTAB, a plot of λ DNA/HindIII fragment size versus signal intensity showed a direct linear relationship.

The sensitivity of the dyes was assayed by running a number of loads of λ DNA/HindIII fragments complexed to dye at a constant ratio. Fragments stained with TOTAB at 5 bp:dye could be visualized down to 12 pg per band. TOED was less sensitive, for DNA loads of less than 1 ng only the 23 kb fragment was detectable when stained with TOED at 5 bp:dye. The 23 kb λ DNA/HindIII fragment band stained with TOED at 2 bp:dye was detectable down to 380 pg. Studies of time-dependence of band intensity for TOED-stained λ DNA/Hind III fragments indicated slow dissociation of the dye in the course of electrophoresis.

Gel electrophoresis of mixtures of varying amounts of λ DNA/Hind III fragments with a constant amount of the dye was performed with TOTAB and TOED. For TOTAB, the band fluorescence intensity, calculated per mole of dye, was constant for DNA dye ratios of 100 to 20 bp:dye and saturated at 4–5 bp:dye.

The dependence of fragment mobility on DNA:dye ratio was explored for TOTAB. Standardized to a mobility of 1 for the fragments loaded with dye at 100 bp:dye, mobility at 50 bp:dye was 1, at 20 bp:dye 0.99, at 10 bp:dye 0.97, and at 5 bp:dye 0.92.

Complexes of FED with dsDNA were found to be more stable to electrophoresis than complexes of dsDNA with ethidium bromide.

MULTIPLEX DETECTION AND SIZING OF dsDNA FRAGMENTS

A two-color multiplex experiment employing a 1 kb dsDNA ladder complexed with TOTAB run together with λ DNA/HindIII fragments complexed with thiazole orange dimer was performed. A least squares fit of the mobilities of the 1 kb ladder bands complexed with TOTAB plotted against the inverse log of size of the fragments allowed determination of the size of the λ DNA/HindIII fragments stained with TOTO with a precision of 2% or better.

It is evident from the above results that the subject invention provides unique opportunities for detecting a wide variety of molecules in numerous different environments. Of particular interest, is the ability to use a single light source of narrow wavelength bandwidth to excite a plurality of molecules, where each of the molecules can be detected independently. Furthermore, by intercalating the subject dyes with DNA, the fluorescence yield is greatly enhanced.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A multiplex fluorescence analysis kit comprising:
   at least two fluorescent multimers, each multimer having at least two fluorophores, at least one of said multimers characterized by:
   a) comprising at least two different fluorophores, which fluorophores absorb and emit at different wave lengths when bound to dsDNA;
   b) having a Stokes shift of at least about 25 nm;
   c) capable of intercalating dsDNA at a ratio of at least one dye per 200 bp;
   d) having from 2 to 4 fluorophores; wherein said fluorescent multimers can be excited within the same narrow light bandwidth range of not more than about 30 nm when bound to dsDNA, and have emission maxima at least 25 nm apart.

2. A kit according to claim 1, wherein said at least two fluorescent multimers have said fluorophores joined by a linking chain comprising at least two positive charges.

3. A kit according to claim 1, wherein said kit comprises at least three multimers.

* * * * *